(12) United States Patent
Papakonstantinou et al.

(10) Patent No.: US 10,003,945 B2
(45) Date of Patent: Jun. 19, 2018

(54) SYSTEMS AND METHODS FOR REAL TIME DETECTION AND REPORTING OF PERSONAL EMERGENCIES

(71) Applicant: MOBILTRON, INC., Piraeus (GR)

(72) Inventors: Vassilis Papakonstantinou, Piraeus (GR); Stavros Schizas, Athens (GR)

(73) Assignee: MOBILTRON, INC., PIRAEUS (GR)

( * ) Notice: Subject to any disclaimer, the term of this patent is extended or adjusted under 35 U.S.C. 154(b) by 133 days.

(21) Appl. No.: 14/939,678

(22) Filed: Nov. 12, 2015

(65) Prior Publication Data

US 2016/0142894 A1 May 19, 2016

Related U.S. Application Data

(60) Provisional application No. 62/079,170, filed on Nov. 13, 2014.

(51) Int. Cl.
*H04W 4/02* (2018.01)
*H04W 4/22* (2009.01)
(Continued)

(52) U.S. Cl.
CPC ............. *H04W 4/22* (2013.01); *A61B 5/00* (2013.01); *A61B 5/0022* (2013.01);
(Continued)

(58) Field of Classification Search
CPC .................................................. H04W 4/22
See application file for complete search history.

(56) References Cited

U.S. PATENT DOCUMENTS 6,579,231 B1 6/2003 Phipps
2008/0001735 A1 1/2008 Tran
(Continued)

FOREIGN PATENT DOCUMENTS

EP 0 987 047 A2 3/2000

OTHER PUBLICATIONS

International Search Report and Written Opinion of the International Searching Authority for PCT/IB2015/058759 dated Apr. 5, 2016.
(Continued)

*Primary Examiner* — Mazda Sabouri
(74) *Attorney, Agent, or Firm* — Foley & Lardner LLP; Christopher J. McKenna

(57) ABSTRACT

According to at least one aspect, a system and corresponding method for detecting and reporting personal emergency events includes a mobile application running on a client device of a user and a backend application running on a backend system. The mobile application and the backend application can communicate on a regular basis. The mobile application or the backend application can regularly monitor sensor data, user contextual data or other data indicative of user state of health, activities or environment and detect or predict an emergency event of the user based on the monitored data. Upon detecting an emergency event, the mobile application or the backend application can warn the user or notify emergency contacts of the user of the emergency event. The backend application can use the sensor data or other user data to update an emergency predictive model specific to the user employed to detect or predict emergency events.

16 Claims, 11 Drawing Sheets

(51) Int. Cl.
*A61B 5/00* (2006.01)
*G06F 19/00* (2018.01)
*G08B 21/04* (2006.01)
*A61B 5/0205* (2006.01)
*A61B 5/11* (2006.01)

(52) U.S. Cl.
CPC ..... *G06F 19/3418* (2013.01); *G08B 21/0453* (2013.01); *G16H 50/20* (2018.01); *H04W 4/023* (2013.01); *H04W 4/90* (2018.02); *H04W 76/50* (2018.02); *A61B 5/02055* (2013.01); *A61B 5/1112* (2013.01); *A61B 5/747* (2013.01)

(56) References Cited

U.S. PATENT DOCUMENTS

| | | | |
|---|---|---|---|
| 2008/0166992 A1 | 7/2008 | Ricordi et al. | |
| 2012/0282887 A1* | 11/2012 | Khoo | G08G 1/205 455/404.2 |
| 2013/0060167 A1* | 3/2013 | Dracup | A61B 5/11 600/595 |
| 2015/0038109 A1* | 2/2015 | Salahshour | H04W 4/22 455/404.2 |
| 2016/0071392 A1 | 3/2016 | Hankey et al. | |

OTHER PUBLICATIONS

Partial International Search Report on PCT/IB2015/058759, dated Jan. 28, 2016.

\* cited by examiner

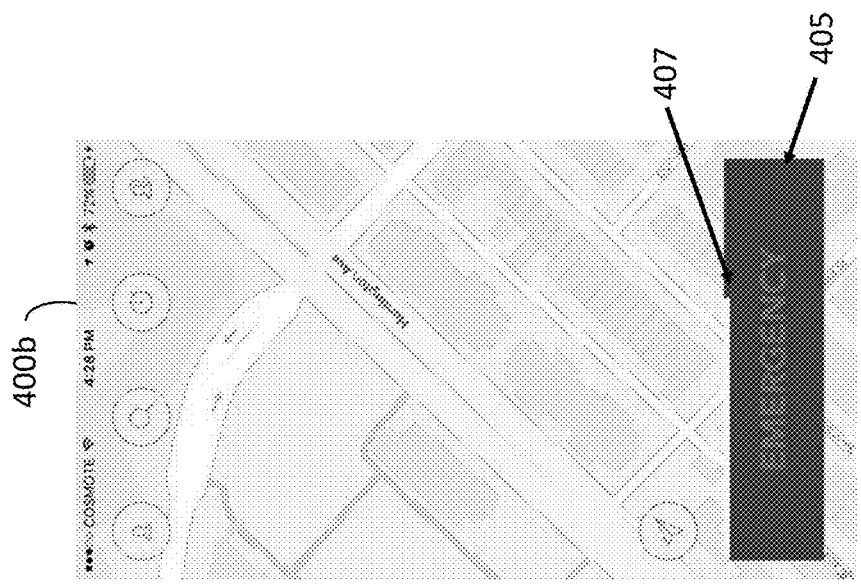

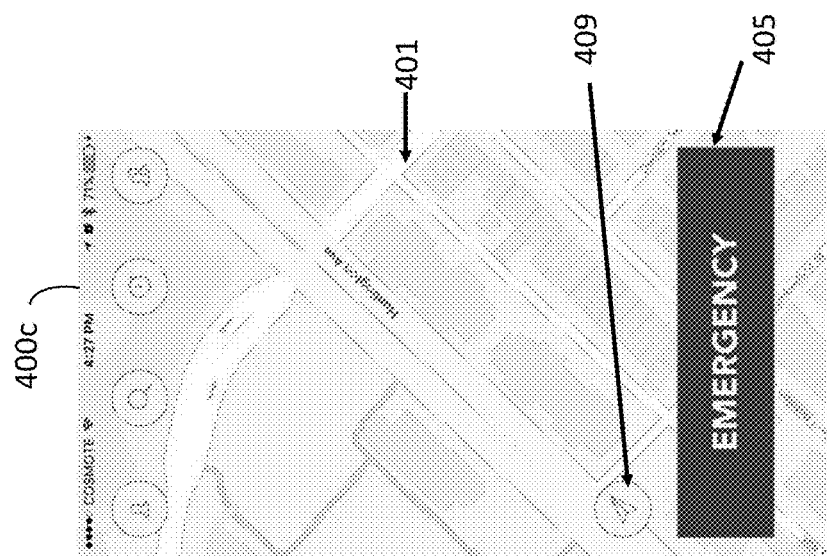

SYSTEMS AND METHODS FOR REAL TIME DETECTION AND REPORTING OF PERSONAL EMERGENCIES

RELATED APPLICATION

This application claims the benefit under 35 U.S.C. § 111(b) of U.S. Provisional Application No. 62/079, 170, entitled "SYSTEMS AND METHODS FOR REAL TIME DETECTION AND REPORTING OF PERSONAL EMERGENCIES" and filed on Nov. 13, 2014, which is incorporated herein by reference in its entirety.

FIELD OF THE DISCLOSURE

The present application relates generally to detecting and reporting emergency events associated with individuals, more particularly, to methods and systems for monitoring and analyzing users health data via mobile devices to detect and report users emergency events.

BACKGROUND

As people carry out their daily routine activities, they take risks that they usually underestimate. Whether driving a car, crossing a road, taking a walk or climbing a mountain, a person performing any of these activities may end up in an accident. For elderly or sick people, they can be the subject of a personal emergency event even when staying at home. In case of personal emergency, detecting such events on time usually allows for fast and proper help or rescue to be provided to the people at risk. However, when a person undergoes a personal emergency while alone or in a secluded location, detecting the emergency event by others may become less likely, and, therefore, the person is less likely to receive proper help on time. Furthermore, research has shown that when many people witness an emergency event, they very often assume somebody else will call to report the emergency event to emergency service providers (e.g., police, fire department, hospital, etc.). Such behavior reduces the probability of a timely report of an incident, to some extent, by an amount proportional to the number of people witnessing the emergency event.

Some existing emergency detection/response systems make it easier for a person undergoing a personal emergency at home to seek help. For example, the personal emergency response system (PERS) provides a device that can be connected to an emergency switchboard through a phone line. A person undergoing a personal emergency event at home (such an elderly or sick person falling while alone) can initiate a call for help by pressing a button on such a device.

SUMMARY

The present disclosure relates to methods and systems for detecting and reporting personal emergency events via a mobile application running on a client device of a user. The systems and methods described herein allow detection of emergency event(s) associated with the user based on regularly collected sensor data, user contextual data and/or other data relevant to the state of health, activities, and environment of the user. In one aspect, systems and methods described herein include the mobile application and a corresponding backend application running on a backend system. The mobile application and the corresponding backend application can be configured to communicate on a regular basis. The mobile application or the backend application can be configured to regularly monitor sensor data, user contextual data, and/or other data indicative of states of the health, activities or environment of the user. Based on the monitored data, the mobile application or the backend application can be configured to determine whether or not the user is undergoing, or about to undergo, an emergency event using an emergency predictive model. Upon detecting a personal emergency event, the mobile application or the backend application can warn the user or notify emergency contacts of the user of the personal emergency event. The mobile application can be configured to forward the sensor data and other data relevant to the states of the health, activities or environment of the user to the corresponding backend application. The backend application can use the data received from the mobile application and other data obtained from other sources to generate, or update, an emergency predictive model specific to the user. The backend application can provide the generated emergency predictive model or parameters thereof to the mobile application for use in detecting personal emergency events associated with the user. In some embodiments, the backend application can use the generated emergency predictive model or parameters thereof to detect personal emergency events associated with the user.

In some implementations, the sensor data can be associated with sensors integrated in the client device of the user (such as accelerometer(s), gyroscope(s), digital compass, microphone(s), camera(s), or the like), sensors mounted on wearable articles of the user (such as thermometer(s), pulse measuring device(s), pulse oximetry, accelerometer(s), gyroscope(s), camera(s), or the like) ambient sensors (such as thermometer(s), humidity measuring device(s) or the like), sensors associated with medical devices (such as batteries chargeability level detection device(s), heart beat detection device(s) or the like), other sensors or a combination thereof. The data monitored by the client application can include user health data (such as user pulse data, user temperature data, user blood sugar readings, user blood pressure readings or the like), ambient data (such as ambient temperature, ambient humidity, weather alerts, or the like), user activities data (such as type of activity, user motion data, user location data or the like).

In some implementations, the mobile application or the backend application can be configured to detect an impending emergency event or a current (or immediate) emergency event. The mobile application or the backend application can be configured to warn the user of the client device or an emergency contact of the user when an impending emergency event is detected. Warning the user (or another person) can include providing information about the detected impending emergency event or action(s) to be taken by (or for) the user. In the case of a detected current emergency event, the mobile application or the backed application can be configured to notify one or more emergency contacts of the user of the detected emergency event. Notifying the emergency contacts can include sending message(s) with information indicative of the detected emergency event, the latest recorded location of the user, information indicative of any relevant medical information of the user or a combination thereof. The mobile application can also be configured to display detected emergency event information, user medical information or other user information on a screen of client device. The mobile application can further lock the screen of the client device with the displayed information. The mobile application or the backend application can be configured to notify an emergency responsive service of the detected emergency event and the location of the user.

In some implementations, the backend application can be configured to receive data collected by the corresponding mobile application and data obtained from other online sources. The backend application can be configured to customize the emergency predictive model and parameters thereof based on obtained user-related data. The backend application can send data indicative of the customized predictive model or the parameters thereof to the corresponding mobile application or use the customized emergency predictive model to detect or predict emergency events. The adaptation/customization of the emergency predictive model on a regular basis by the backend application allows accurate detection of emergency events for the user. The backend application can be further configured to exchange user-related data with healthcare provider services or social network services. The backend application also can obtain user-related data from web services such as online weather services, online news services, government web sites or the like. In some implementations, the backend application can be configured to forward information indicative of detected emergency events to a call center associated with the backend system or to an emergency responsive service system.

In some implementations, the backend application can be configured to encrypt user data with user specific credentials. The backend application can execute processes for customizing the emergency predictive model of the user on a micro virtual machine (mVM). In some implementations, the backend application can monitor availability of the corresponding mobile application and launch the mVM when detecting the corresponding mobile application being started on the client device. The mVM can be executed on a micro virtual server with a time-varying Internet Protocol (IP) address in order to guarantee the privacy and security of user's data. Upon detecting that the corresponding mobile application is turned off on the client device, the backend application can halt the mVM, encrypt an image of the mVM and other user data and store the encrypted data for use when the corresponding mobile application is turned on again on the user's client device. The use of the mVM enhances security and privacy of user data. The user can export corresponding data from the backend system with little or no risk of breaching user privacy by others. If the user decides to delete the corresponding data from the backend system, the mVM with the user's encrypted data will be deleted permanently with no copies left on the backend system, therefore, avoiding (or mitigating) the risk access of the user data by others.

According to at least one aspect, a method for detecting an emergency occurring to a user can include a mobile device receiving data about at least one of a health, an activity or an environment of the user. The method can include the mobile device or a server analyzing the data about at least one of a health, an activity or an environment of the user and detecting from the analyzed data an emergency event associated with the user. The method can also include the mobile device or the server executing, responsive to the detection, an emergency protocol.

In some embodiments, the method can include the mobile device receiving data from one or more sensors about one or more of motion, location, ambient temperature, ambient humidity, medical measurements of the user. The method can include receiving from one or more content sources via one or more networks contextual data about the user. The contextual data can include one or more of the following: traffic patterns associated with location of the user, air pollution level associated with the location of the user, prior activity of the user, and posts, messages or change of status in content of a user feed of the user. The method can include the mobile device receiving data about public alerts related to one of a location or the activity of the user, the data about public alerts comprising one or more of the following: disaster alerts, weather alerts, crime alerts, bacteria or virus alerts, infectious disease alerts.

In some embodiments, the method can include the mobile device or the server using an emergency predictive model for analyzing the data to take into account current condition of the user, environment parameters, user settings and past knowledge to estimate the probability of an emergency event. The mobile device or the server can compute a score value indicative of a likelihood of an emergency event occurring to the user. The mobile device or the server can compare the score value to a given threshold value. The mobile device or the server can detect the emergency event responsive to the score value being greater than the given threshold value.

In some embodiments, the method can include verifying the emergency event via the mobile device. The method can also include the mobile device or the server initiating responsive to verification, emergency reporting. The method can include the mobile device or the server sending, responsive to the verification, a distress signal to one or more of emergency contacts of the user, an emergency response service or an ad-hoc safety network created by the user.

According to at least one aspect, a system for detecting an emergency occurring to a user can include an application configured to be executable on a mobile device and a server. The application can receive data about at least one of a health, an activity or an environment of the user. The server can be configured to communicate with the mobile application and receive data from the mobile device. At least one of the mobile application or the server can be configured to analyze the data about at least one of a health, an activity or an environment of the user, detect from the analyzed data an emergency event associated with the user, and execute, responsive to the detection, an emergency protocol.

In some embodiments the data can be received from one or more sensors comprises one or more of the following: motion, location, ambient temperature, ambient humidity and medical measurements of the user. The data can be received from one or more content sources via one or more networks and can include contextual data about the user. The contextual data can include one or more of the following: traffic patterns associated with location of the user, air pollution level associated with the location of the user, prior activity of the user, and posts, messages or change of status in content of a user feed of the user. At least one of the mobile application or the server can be configured to receive data about public alerts related to one of a location or the activity of the user, the data about public alerts comprising one or more of the following: disaster alerts, weather alerts, crime alerts, bacteria or virus alerts, infectious disease alerts.

In some embodiments, at least one of the mobile application or the server can be configured to use an emergency predictive model for analyzing the data to take into account current condition of user, environment parameters, user settings and past knowledge to estimate the probability of an emergency event. The mobile device or the server can compute a score value indicative of a likelihood of an emergency event occurring to the user. The mobile device or the server can compare the score value to a given threshold value. The mobile device or the server can detect the emergency event responsive to the score value being greater than the given threshold value.

In some embodiments, at least one of the mobile application or the server can be configured to verify the emergency event via the mobile device. The mobile application or the server can initiate, responsive to verification, emergency reporting. The mobile application or the server can send, responsive to the verification, a distress signal to one or more of emergency contacts of the user, an emergency response service or an ad-hoc safety network created by the user.

In some embodiments, the server can monitor availability of the mobile application and launch a micro-virtual machine (mVM) upon detecting that the mobile application is started on the mobile device. The server can halt the mVM, upon detecting that the mobile application is turned off on the mobile device and encrypt an image of the mVM and data associated with the user of the mobile device data. The server can store the encrypted data for use when the corresponding mobile application is turned on again on the mobile device. The mVM can be executed on a micro-virtual server and an Internet protocol (IP) address of the micro-virtual server can randomly set at initiation. The micro-virtual server can be renewed at random intervals during a period of time when the mVM is running on the micro-virtual server.

According to at least one aspect, a method for predicting an emergency event that is to occur to a user can include a mobile device receiving data about at least one of a health, an activity or an environment of the user. The method can include the mobile device or the server analyzing the data about at least one of the health, the activity or the environment of the user of the mobile device. The mobile device or the serve can determine from the analyzed data, a score value indicative of a likelihood of an emergency event occurring to the user, and communicate, responsive to the score value being greater than a threshold, a notification to the user to change behavior to avoid the emergency event.

In some embodiments, the method can include the mobile device or the server detecting, that the behavior of the user did not change and responsive to the detecting initiating, by one of the mobile device or the server, emergency reporting. The method can also include the mobile device or the server sending a distress signal to one or more of the following: emergency contacts of the user, an emergency response service or an ad-hoc safety network created by the user. In some embodiments, the data can include contextual data about the user and data from one or more sensors associated with the user.

According to at least one aspect, a system for predicting an emergency event is to occur to a user can include a mobile application configured to be executable on a mobile device and a server configured to communicate with the mobile application and receive data from the mobile device. The mobile application can be configured to receive data about at least one of a health, an activity or an environment of the user. The mobile application or the server can be configured to receive data about at least one of a health, an activity or an environment of the user. The mobile application or the server can be configured to analyze the data about at least one of the health, the activity or the environment of the user of the mobile device. The mobile application or the server can be configured to determine, from the analyzed data, a score value indicative of a likelihood of an emergency event occurring to the user. The mobile application or the server can be configured to communicate, responsive to the score value being greater than a threshold, a notification to the user to change behavior to avoid the emergency event.

In some embodiments, the mobile application or the server can be configured to detect that the behavior of the user did not change and responsive to the detecting initiating, by one of the mobile device or the server, emergency reporting. The mobile application or the server can be configured to send responsive to the detection a distress signal to one or more of the following: emergency contacts of the user, an emergency response service or an ad-hoc safety network created by the user. In some embodiments, the data can include contextual data about the user and data from one or more sensors associated with the user.

BRIEF DESCRIPTION OF THE DRAWINGS

FIGS. 4A-4D are screenshots depicting a user interface of a client application for detecting and reporting personal emergencies.

DETAILED DESCRIPTION

For purposes of reading the description of the various embodiments below, the following descriptions of the sections of the specification and their respective contents may be helpful:

Section A describes a network environment and computing environment which may be useful for practicing embodiments of detecting and reporting personal emergencies.

Section B describes embodiments of systems and methods for generating and using codes integrated on articles of manufacture for initiating or executing a transaction.

A. Computing and Network Environment

In addition to discussing specific embodiments of generating and using codes integrated on articles of manufacture for initiating or executing a transaction it may be helpful to describe aspects of the operating environment as well as associated system components (e.g., hardware elements) in connection with the methods and systems described herein.

Figure 1A:
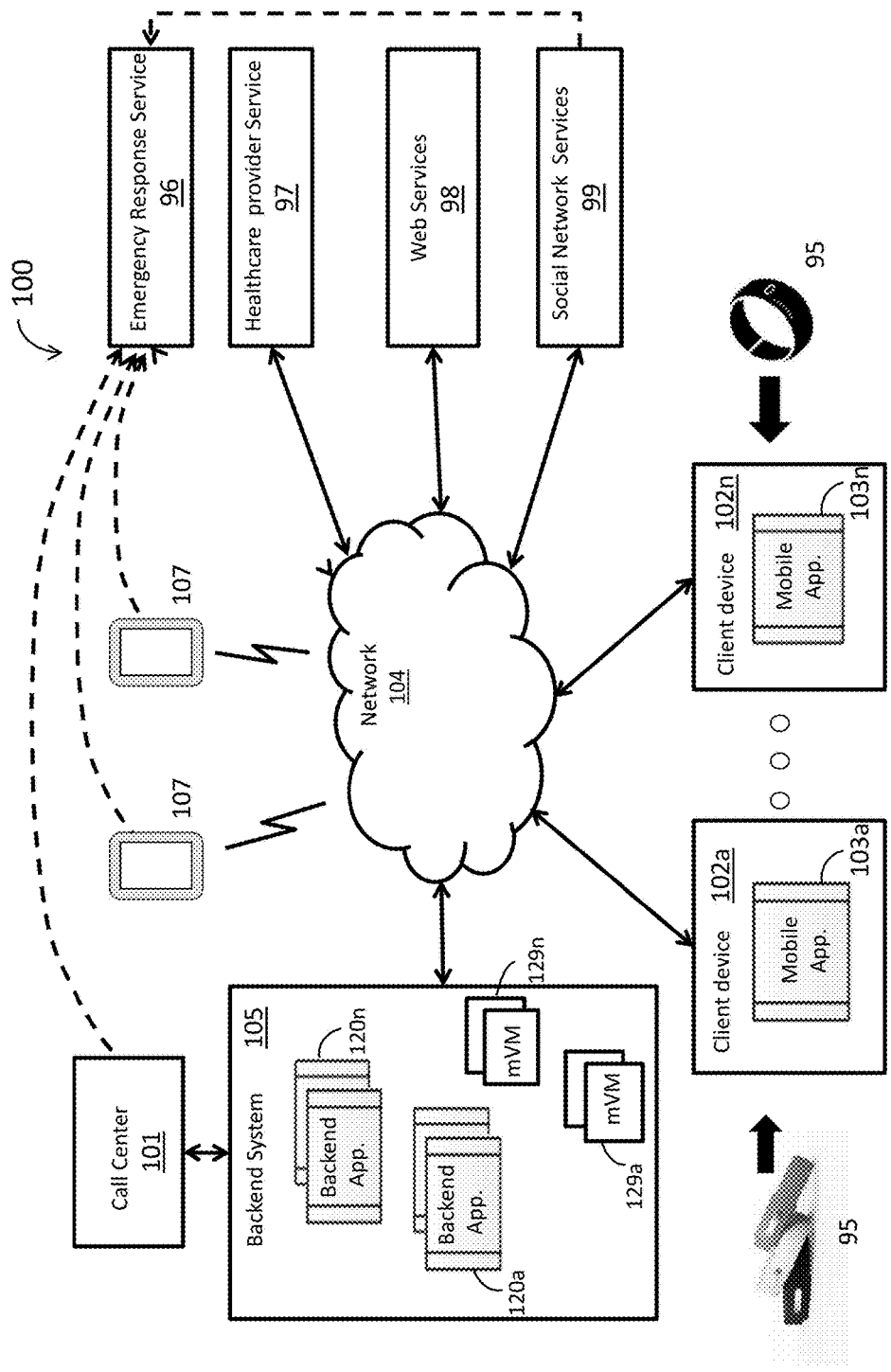
FIG. 1A is a diagram depicting an embodiment of a network environment for detecting and reporting personal emergencies.

FIG. 1A is a diagram depicting an embodiment of a network environment 100 for detecting and reporting personal emergencies. In brief overview, the network environment 100 includes one or more client devices 102a-102n (also generally referred to as local machine(s) 102, client(s) 102, client node(s) 102, client machine(s) 102, client computer(s) 102, client device(s) 102, endpoint(s) 102, or endpoint node(s) 102) configured to execute one or more corresponding mobile applications 103a-103n (also generally referred to as client application(s) 103), a backend system 105 configured to execute a plurality of backend applications 120a-120n, one or more emergency contact devices 107 (also generally referred to as emergency contact node(s) 107 or emergency contact(s) 107), one or more call centers 101, one or more communication networks, and systems associated with services such as emergency response service(s) 96, healthcare provider service(s) 97, web service(s) 98, or social network service(s) 99. The client devices 102 can be configured to receive sensor data from sensors mounted on wearable articles 95, such as pieces of jewelry or other accessories. Executing the one or more backend applications 120a-120n can include executing one or more micro virtual machines (mVMs) 129a-129n (also referred to as mVM 129).

The client device 102, the backend system 105, and the emergency contact devices 107 can be coupled to the one or more networks 104, and can communicate with each other through the one or more networks 104. In some implementations, the backend system 105, or the client device 102, also can be configured to communicate with the systems associated with the healthcare provider service(s) 97, the web service(s) 98 and the social network service(s) 99 through the one or more networks 104. The backend system 105, or the client device 102, may be further configured to automatically communicate with the system(s) associated with the emergency response service(s) 96 through the one or more networks 104. The one or more networks 104 provide wired and/or wireless communication links between devices (such as client devices 102, computer devices associated with the backend system 105, emergency contact devices 107, and/or electronic devices associated with the emergency responsive service 96, the healthcare provider service(s) 97, the web service(s) 98 or the social network service(s) 99) coupled thereto. Example embodiments of the networks 104 and devices coupled thereto are described in further details with respect to FIGS. 1B-1E in terms of hardware and software. In some implementations, the one or more call centers 101 are associated with, or communicatively coupled with, the backend system 105.

The client device 102 can include a corresponding client application 103 running thereon for monitoring and reporting emergency events associated with the user of the client device 102. The mobile application 103 can be configured to monitor and analyze sensor-measured data obtained from one or more sensors, user contextual data, or other data obtained from other sources. The one or more sensors can include sensor(s) integrated in the client device 102, sensor(s) mounted on wearable article(s) 95, ambient sensor(s), sensor(s) associated with a medical device, other sensors, or a combination thereof. The sensors allow continuous and non-invasive logging of accurate health data of the user, ambient data or other types of data. The client device 102 can communicate with the sensors through a BLUETOOTH® link, a near field communication (NFC) link, a Wi-Fi communication link, other communication link or a combination thereof. Data obtained from other sources can include data obtained from the backend system 105, the healthcare provider service(s) 97, the web service(s) 98 or a combination thereof.

Based on the analysis of the obtained data, the mobile application 103 can detect an emergency event associated with the user of the client device 102. Upon detecting an emergency event, the mobile application 103 can cause the client device 102 to take proper action(s), such as warning the user through output signals or communicating with the emergency contact device(s) 107 associated with emergency contact individual(s) for the user. The emergency contact individual(s) can communicate with the emergency responsive service 96, for example, through the corresponding device 107 and the one or more network 104, upon receiving notification(s) of an immediate emergency event from client device 102. The client device 102 may further automatically notify the emergency responsive service 96 of a detected immediate emergency event, for example, through electronic messages. The client device 102 and the mobile application 103 running thereon can be configured to store collected sensor-measured data, user contextual data, and other personal data of the user at least temporarily. The collected sensor-measured data can be transmitted by the client device 102 and the mobile application 103 running thereon to the backend system 105 for permanent storage.

The backend system 105 can include a computer system configured to execute a plurality of backend applications 120. In some implementations, each mobile application 103 running on a user's client device 102 is associated with a corresponding backend application 120 running on the backend system 105. The backend application 120 and the corresponding mobile application 103 are configured to communicate regularly to exchange data. In some implementations, the backend application 120 and the corresponding mobile application 103 communicate over a secure communication protocol such as the Hypertext Transfer Protocol Secure (HTTPS), the Secure Real-time Transport Protocol (SRTP), the Secure Communications Interoperability Protocol (SCIP), or other secure communication protocols known to a person of ordinary skill in the art.

The backend application 120 can be configured to generate emergency predictive model(s) for use by the corresponding mobile application 103 in analyzing emergency events of the corresponding user. The generated emergency predictive model(s) or parameters thereof are provided by the backend application 120 (through the backend system 105, the one or more networks 104 and the client device 102) to the corresponding mobile application 103. The backend application 120 can provide other information to the corresponding mobile application such as medical data acquired from the healthcare provider service(s) 97, weather information or public alerts acquired from the web service(s) 98, user contextual data, other information obtained from the social network service(s) 99, or a combination thereof. In some implementations, the backend application 120 can be configured to launch a mVM 129 upon receiving an indication that the mobile application 103 is launched on the client device 102. The mVM 129 is configured to execute user-related processes or algorithms. The user-related processes or algorithms can include a process to generate a user-customized emergency predictive model or a process to detect emergency events. The use of the mVM 129 can enhance data security and user data privacy.

The backend application 120 also can be configured to receive sensor data, user personal data, user contextual data, or other data collected by the client device 102 associated with the corresponding mobile application 103. The backend application 120 can be configured to store the received sensor data, user personal data, user contextual data, or other data for use in tracking the state of health of the corresponding user and generating/updating user-specific emergency predictive model(s). As such, the backend system 105 can act as a repository for storing users data. The backend application 120 can be configured to mirror one or more functionalities of the corresponding client application 103. The backend application 120 can also be configured to monitor and analyze sensor data, user contextual data, or other data to detect and report emergency events. For instance, when communication connection between the mobile device 102 and the backend system 105 is lost but there is data to indicate that there may be an emergency event, the backend application 120 can analyze the available data to detect the presence of a current emergency event or an impeding emergency event. If an emergency event is detected, the backend application 120 can report the detected emergency event or take other actions in response to such detection. In some implementations, the backend system 105 and the backend application 120 can be coupled to the call center 101. When an emergency event is detected, emergency event information or other user information can be forwarded to the call center 101. Operators in the call center 101 can verify the emergency event with the user, for example, by contacting the user. The operators can also contact the emergency responsive service(s) 96 or emergency contacts of the user.

Each user associated with a client device 102 and a mobile application running thereon can have an emergency contact network including one or more individuals (or entities) and one or more corresponding emergency contact devices 107. The client device 102 can also be configured to act as emergency contact device 107 for another user. An emergency contact device 107 can also be configured to act as client device 102 for another user. That is, a user associate with a client device 102 can be an emergency contact of another user. The mobile application 103 or the corresponding backend application 120 can be configured to send emergency event notifications to the emergency contact devices 107 if an emergency event is detected. The emergency event notification can include description of the emergency event, an indication of a location of the client device 102, medical information of the user of the client device 102, other information or a combination thereof. The emergency contact individuals can contact the emergency responsive service 96 if an emergency event notification is received. The emergency responsive service 96 can be associated with a government agency, hospitals, a firefighting department, or other entities providing emergency responsive services.

The healthcare provider service(s) 97 can be associated with a pharmacy, hospital(s), or other healthcare providing entities. For instance, the backend application 120 (or the corresponding mobile application 103) can obtain data from a pharmacy system regarding prescriptions or medications associated with the user. The backend application 120 (or the corresponding mobile application 103) can exchange information with a computer system associated with a doctor or other healthcare provider entity associated with the user.

The web service(s) 98 can include web pages providing weather information, public alerts (such as hurricane, storm or tornado alerts, virus and infectious disease alerts, crime alerts, other public alerts or a combination thereof), news or a combination thereof. The mobile application 103 can obtain, either directly or via the corresponding backend application 120, information from the web service(s) 98 for use in assessing any impending or immediate emergency event for the user. The information obtained from the web service(s) 98 can be filtered by the backend application 120 based on user's location or other information.

The social network service(s) 99 can include social network services to which the user of the client device 102 is subscribed. Some user information (such as login/logout time, location information, or other information) can be automatically shared with one or more social network contacts of the user. For instance such information can be automatically shared (based on user's preferences) with family members, friends, emergency contacts, or other contacts subscribed to the same social network service(s) 99. The shared information, can allow one or more individuals in the social network of the user to remotely monitor the user's activities. The user of the client device 102 can also check, via information acquired from the social network service(s) 99, activities of friends. The backend application 120 or the corresponding client application 103 can allow automatic retrieval of data from the social network service(s) 99 and presenting that information to the user. Also, the backend application 120 or the corresponding client application 103 can allow automatic publishing/sharing of some user information with social network contacts of the user. The social network service(s) 99 can be configured to forward an emergency event message indicative of a detected current emergency event (received from a client device 102 or backend application 120) to the emergency response service 96.

Hardware and software implementations of the one or more networks 104 and the devices coupled thereto (such as the client devices 102, devices/serves associated with the backend system 105, the emergency contact devices 107 and servers/devices associated with the services 96-99) are described in further details in FIGS. 1B-1E. Processes for detecting and reporting emergency events are discussed in the following in relation to FIGS. 2-3.

Figure 1B:
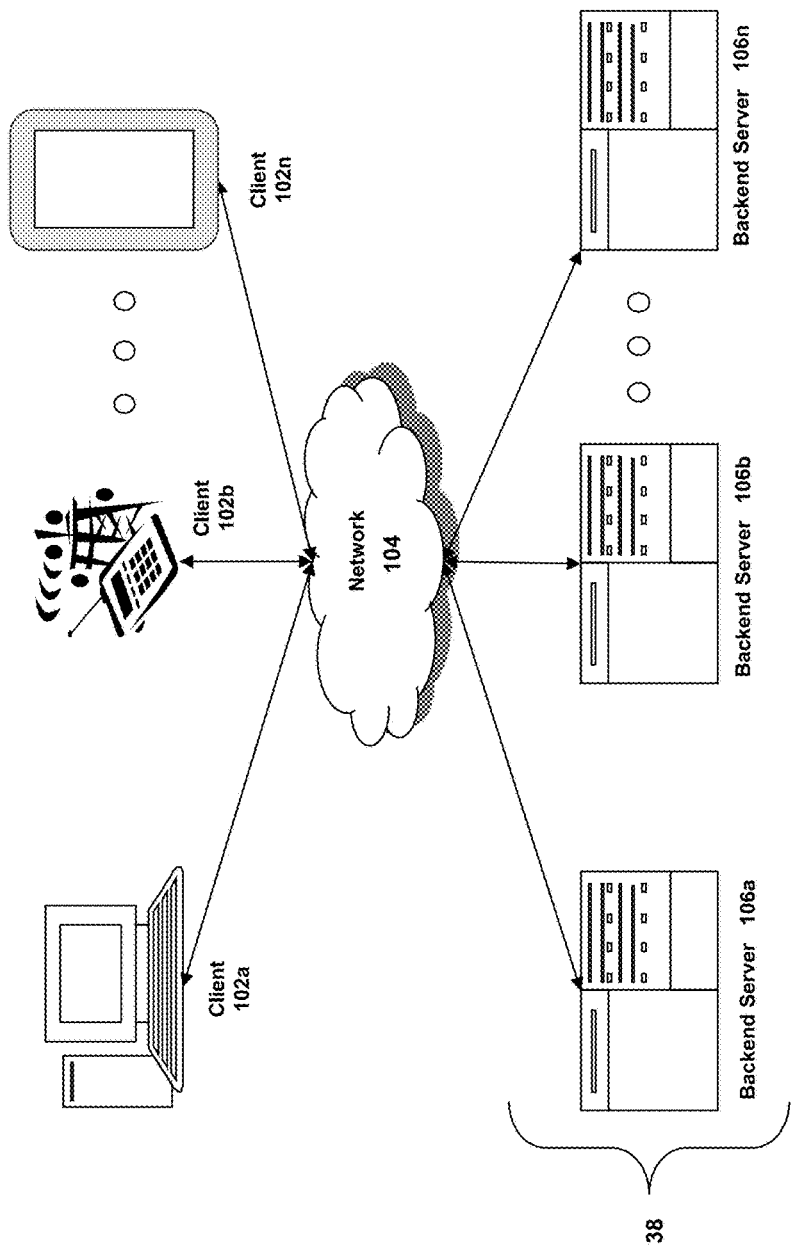
FIG. 1B is a block diagram depicting an embodiment of a network environment comprising local devices in communication with remote devices.

Referring to FIG. 1B, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more backend servers 106a-106n (also generally referred to as backend server(s) 106, backend node 106, or backend remote machine(s) 106) associated with the backend system 105 via one or more networks 104. In some embodiments, a client 102 has the capacity to function as both a client node seeking access to resources provided by a server and as a server providing access to hosted resources for other clients 102a-102n.

Although FIG. 1B shows a network 104 between the clients 102 and the backend servers 106, the clients 102 and the backend servers 106 may be on the same network 104. In some embodiments, there are multiple networks 104 between the clients 102 and the backend servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped backend servers 106. In one of these embodiments, the logical group of backend servers may be referred to as a backend server farm 38 or a backend machine farm 38. In another of these embodiments, the backend servers 106 may be geographically dispersed. In other embodiments, a machine farm 38 may be administered as a single entity. In still other embodiments, the backend machine farm 38 includes a plurality of backend machine farms 38. The backend servers 106 within each backend machine farm 38 can be heterogeneous—one or more of the backend servers 106 or backend machines 106 can operate according to one type of operating system platform (e.g., WINDOWS NT, manufactured by Microsoft Corp. of Redmond, Wash.), while one or more of the other backend servers 106 can operate on according to another type of operating system platform (e.g., Unix, Linux, or Mac OS X).

In one embodiment, backend servers 106 in the backend machine farm 38 may be stored in high-density rack systems, along with associated storage systems, and located in an enterprise data center. In this embodiment, consolidating the backend servers 106 in this way may improve system manageability, data security, the physical security of the system, and system performance by locating backend servers 106 and high performance storage systems on localized high performance networks. Centralizing the backend servers 106 and storage systems and coupling them with advanced system management tools allows more efficient use of server resources.

The backend servers 106 of each backend machine farm 38 do not need to be physically proximate to another backend server 106 in the same backend machine farm 38. Thus, the group of backend servers 106 logically grouped as a backend machine farm 38 may be interconnected using a wide-area network (WAN) connection or a metropolitan-area network (MAN) connection. For example, a backend machine farm 38 may include backend servers 106 physically located in different continents or different regions of a continent, country, state, city, campus, or room. Data transmission speeds between backend servers 106 in the backend machine farm 38 can be increased if the backend servers 106 are connected using a local-area network (LAN) connection or some form of direct connection. Additionally, a heterogeneous backend machine farm 38 may include one or more backend servers 106 operating according to a type of operating system, while one or more other backend servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the backend machine farm 38 may be de-centralized. For example, one or more backend servers 106 may comprise components, subsystems and modules to support one or more management services for the backend machine farm 38. In one of these embodiments, one or more backend servers 106 provide functionality for management of dynamic data, including techniques for handling failover, data replication, and increasing the robustness of the backend machine farm 38. Each backend server 106 may communicate with a persistent store and, in some embodiments, with a dynamic store.

Backend server 106 may be a file server, application server, web server, proxy server, appliance, network appliance, gateway, gateway server, virtualization server, deployment server, SSL VPN server, or firewall. In one embodiment, the backend server 106 may be referred to as a backend remote machine or a backend node.

Figure 1C:
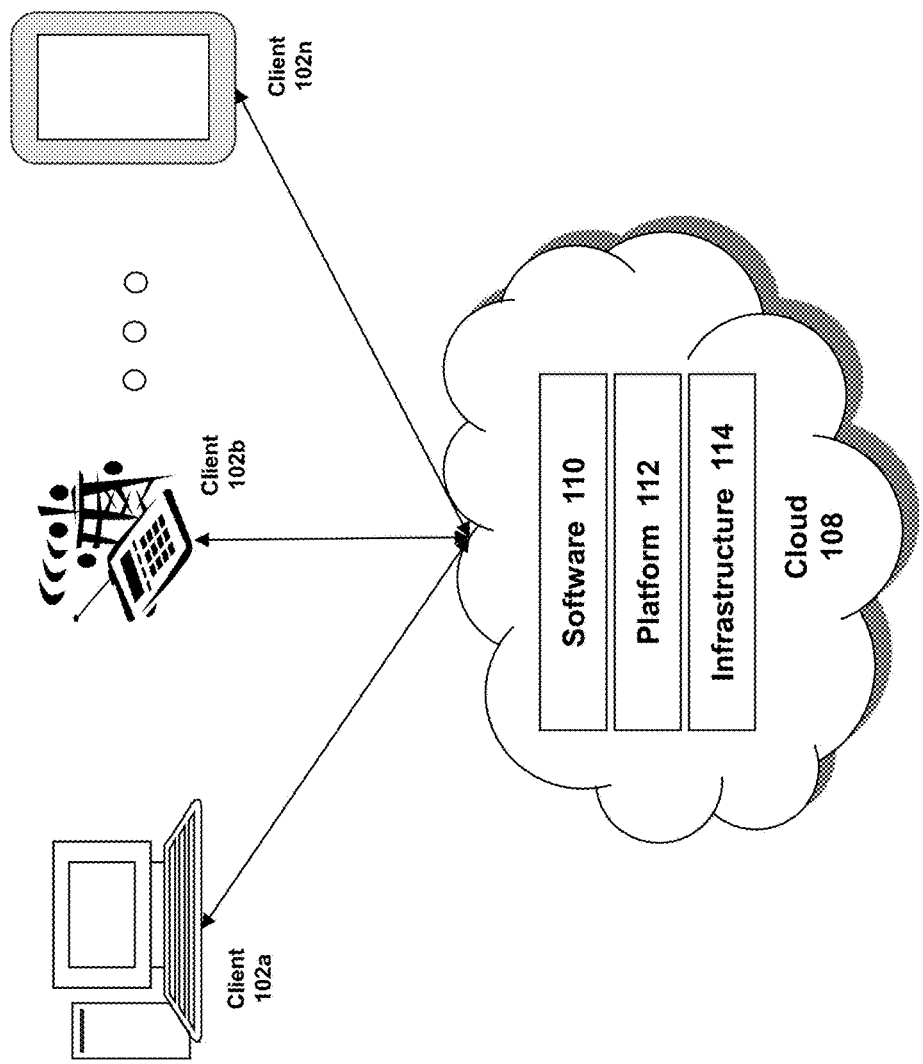
FIGS. 1C-1E are block diagrams depicting embodiments of computers useful in connection with the methods and systems described herein.

Referring to FIG. 1C, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or backend servers 106. A thin client or a zero client may depend on the connection to the cloud 108 or backend server 106 to provide functionality. A zero client may depend on the cloud 108 or other networks 104 or backend servers 106 to retrieve operating system data for the client device. The cloud 108 may include backend platforms, e.g., backend servers 106, storage, backend server farms or data centers.

The cloud 108 may be public, private, or hybrid. Public clouds may include public backend servers 106 that are maintained by third parties to the owners of the owners of the backend application 120. The backend servers 106 may be located off-site in remote geographical locations as disclosed above or otherwise. Public clouds may be connected to the backend servers 106 over a public network. Private clouds may include private backend servers 106 that are physically maintained by owners of the backend applications 120. Private clouds may be connected to the backend servers 106 over a private network 104. Hybrid clouds 108 may include both the private and public networks 104 and backend servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including,e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1D:
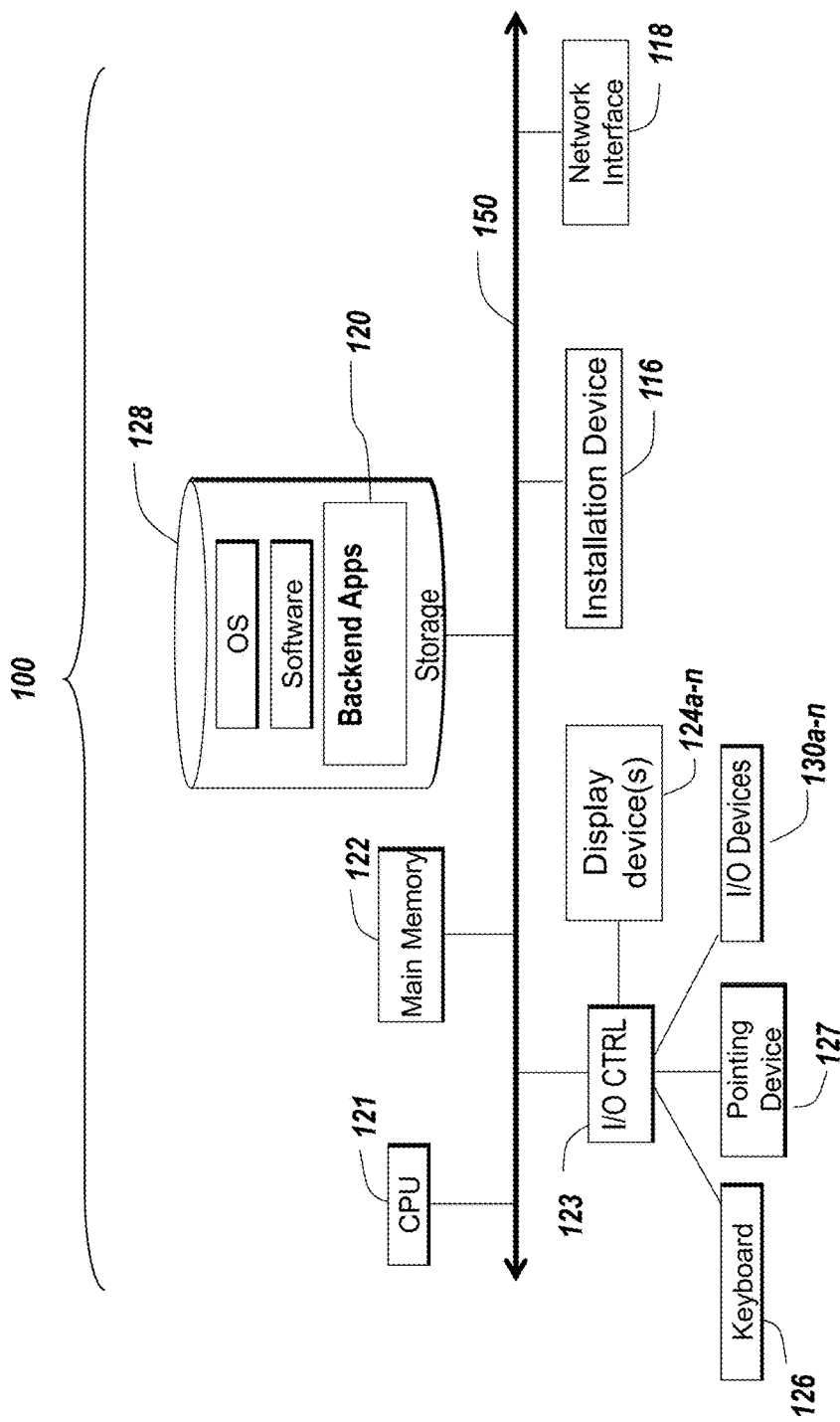
Figure 1E:
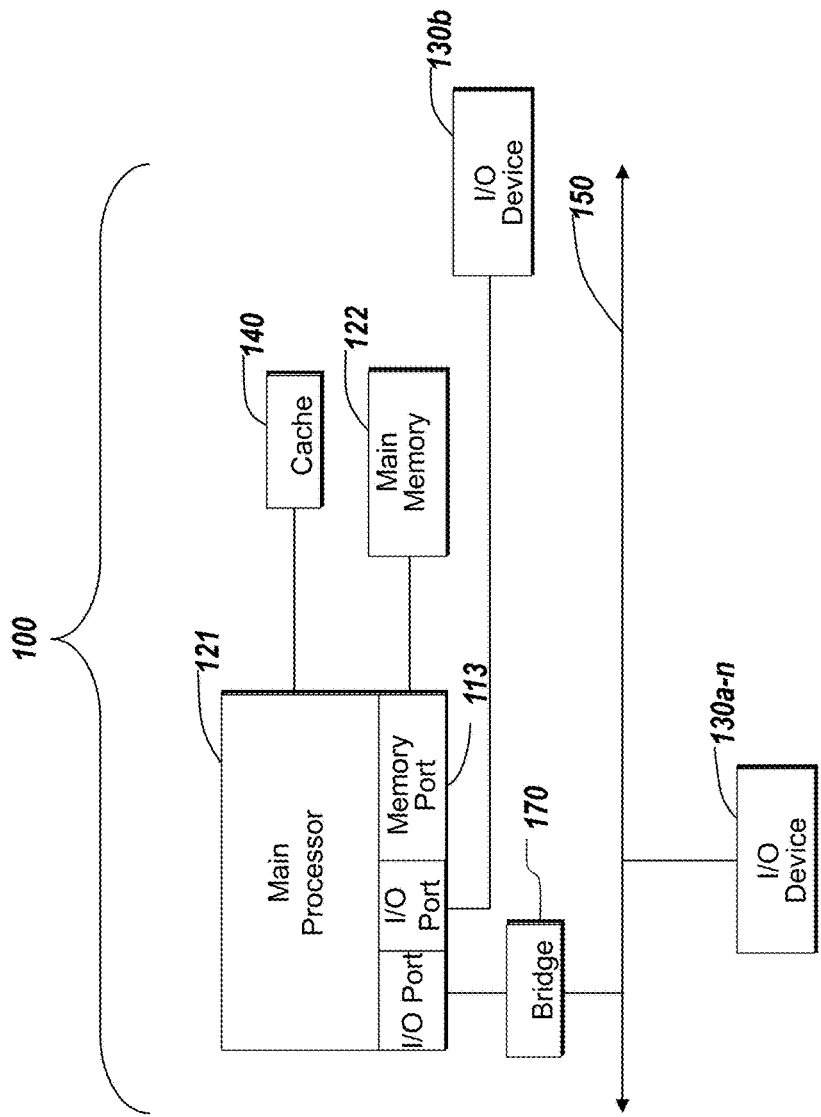

The client 102 and backend server 106 may be deployed as and/or executed on any type and form of computing device, e.g. a computer, network device or appliance capable of communicating on any type and form of network and performing the operations described herein. FIGS. 1D and 1E depict block diagrams of a computing device 100 useful for practicing an embodiment of the client 102 or a backend server 106. As shown in FIGS. 1D and 1E, each computing device 100 includes a central processing unit 121, and a main memory unit 122. As shown in FIG. 1D, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, backend applications 120 or a combination thereof. As shown in FIG. 1E, each computing device 100 may also include additional optional elements, e.g. a memory port 113, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1D, the processor 121 communicates with main memory 122 via a system bus 150 (described in more detail below). FIG. 1E depicts an embodiment of a computing device 100 in which the processor communicates directly with main memory 122 via a memory port 103. For example, in FIG. 1E the main memory 122 may be DRDRAM.

FIG. 1E depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1E, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1E depicts an embodiment of a computer 100 in which the main processor 121 communicates directly with I/O device 130b or other processors 121' via HYPERTRANSPORT, RAPIDIO, or INFINIBAND communications technology. FIG. 1E also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3-D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fiber Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3-D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124*a* for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124*a*-124*n*.

Referring again to FIG. 1D, the computing device 100 may comprise a storage device 128 (e.g. one or more hard disk drives or redundant arrays of independent disks) for storing an operating system or other related software, and for storing application software programs such as any program related to the software 120 for the server 107. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102*a*-102*n* may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1D and 1E may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is a eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Systems and Methods of Detecting and Reporting Emergency Events for Individuals Various embodiments disclosed herein are directed to systems and methods for monitoring and analyzing sensor data to detect and report emergency events for one or more individuals. Detecting and reporting of emergency events for users can be achieved through a platform providing backend applications 120 running on the backend system 105 and mobile applications 103 running on client devices 102 (such as smartphones, tablets, smart watch(es), smart glasses, mobile media devices, etc.) of the users. A mobile application 103 can be downloaded and installed on a client device 102 of a user whose state of health, medical information, activities and/or environment are to be monitored for detecting and reporting emergency events. The mobile application 103 or a corresponding backend application 120 can be configured to monitor and analyze sensor data, user contextual data, or other data to detect and report emergency events. Detected emergency events can be reported to emergency contacts of the user through corresponding emergency contact devices 107.

The backend application 120 can also be configured to monitor and analyze sensor data, user contextual data, or other data to detect and report emergency events. For instance, when communication connection between the mobile device 102 and the backend system 105 is lost but there is data to indicate that there may be an emergency event, the backend application 120 can analyze the available data to detect the presence of a current emergency event or an impending emergency. If an emergency event is detected, the backend application 120 can report the detected emergency event. In some embodiments, the backend application 120 can be configured to mirror the mobile application functionality so that to be able to perform emergency event detection or prediction using whatever data available to the backend system 105. As such, the backend application 120 can take the role of the mobile application 103 in cases where the communication between the mobile device 102 and the backend system 105 breaks down, for instance, due to network coverage or power failure.

During setup of the mobile application 103, the user can be prompted to identify specific emergency contacts or import contacts from an address book or any other database to configure a safety network for the user. Emergency contact information provided to the mobile application 103 can include email addresses, phone numbers, social network information, messaging application(s) information, voice over IP (VoIP) application(s) information, or other information that can be used to communicate with the emergency contact individuals. The user's safety network can include a social safety network configured through existing social networks such as Facebook, Twitter, Foursquare, Google+, the like or a combination thereof. The emergency contacts information can be updated by the user after setup. Once the emergency contacts are identified, the mobile application 103 can notify the emergency contact individuals or entities that they have been assigned as emergency contacts for the user, for example, through instant messaging, social network messaging, email, or other messaging services. The notification to the emergency contacts can include an invitation to join a social safety network for the user. Once a prospective emergency contact has received notification about being assigned as such he/she can either accept or reject the request. If the prospective emergency contact is already a user of the system, the acceptance or rejection of the invitation can take place through the mobile application 103. If the prospective emergency contact is not member of the system, the reply can have the form of a message, an SMS, email or other means associated with the original invitation extended by the user. The social safety network configuration can include authentication of the mobile application 103 or user credentials on the respective social network(s) in order to allow automatic posting of messages by the mobile application 103, taking into consideration the privacy settings of the user.

During the mobile application setup, the client device 102 can prompt the user to enter corresponding medical information such as existing medical conditions, current medication, medical procedures or surgeries performed to the user or other information indicative of the state of health of the user such as user's age, user's weight, etc. The medical information of the user can be used by mobile application 103 or the corresponding backend application 120 to set/adjust a level of emergency sensitivity. For instance, the client device 102 can forward the medical information of the user to the backend system 105 and in response, the corresponding backend application 120 can determine an emergency predictive model customized to the user based on the corresponding medical information. For example, when a user lists heart problems (or a heart disease) as a medical condition, the emergency predictive model customized to the user can be more prone to consider particular situations as emergencies compared to emergency predictive models associated with individuals who do not suffer from heart problems. In some implementations, the mobile application 103 can prompt the user on a regular basis to update the corresponding medical information. Also, the mobile application 103 or the corresponding backend application 120 can receive updates of the user's medical information from other sources such as system(s) associated with the healthcare provider service(s) 97. For example, the mobile application 103 or the corresponding backend application can receive medical diagnosis information, prescription information, or other medical information from a computer system associated with a doctor, hospital or pharmacy. In some implementations the level of emergency sensitivity can be manually set/adjusted by the user to conform to a current activity or state of the user.

The mobile application 103 can further prompt the user to connect the client device 102 with available sensors. Such sensors can include sensors embedded on wearable articles (such as jewelry items, accessories, clothes, etc.), ambient sensors, sensors associated with medical devices (such as pacemaker(s), defibrillator(s), wearable artificial kidney(s), etc.) or the like. Sensors embedded on wearable articles can include motion sensors, thermometer(s), pulse detection sensor(s), pulse oximetry, other sensors or a combination thereof. Sensors associated with medical devices can include sensors to detect batteries level of chargeability, medical sensors or the like. The ambient sensors can include ambient thermometer(s), humidity sensor(s) or other ambient sensors. Connecting the client device 102 with available sensors can include pairing the client device 102 with one or more sensors wirelessly via BLUETOOTH LE, near field communication (NFC) or other wireless communication modes through appropriate handshaking processes. Other communication modes may be employed. In some implementations, connecting the client device 102 with available sensors can include the user entering sensor identification information to the client device 102. The mobile application 103 also can access data from sensors integrated in the client device 102 (such as motion sensors or other sensors).

Once the mobile application 103 is installed and setup on the client device 102, the mobile application 103 can start collecting user-related data, checking for emergency events and communicating with the corresponding backend application 120 on a regular basis. In the following, processes performed by the mobile application 103 and the backend application 120 during deployment phase are discussed. For client devices 102 that have biometric authentication features (such as fingerprint identification capabilities), the mobile application 103, depending on user preferences, may request user fingerprint identification at launch.

Figure 2:
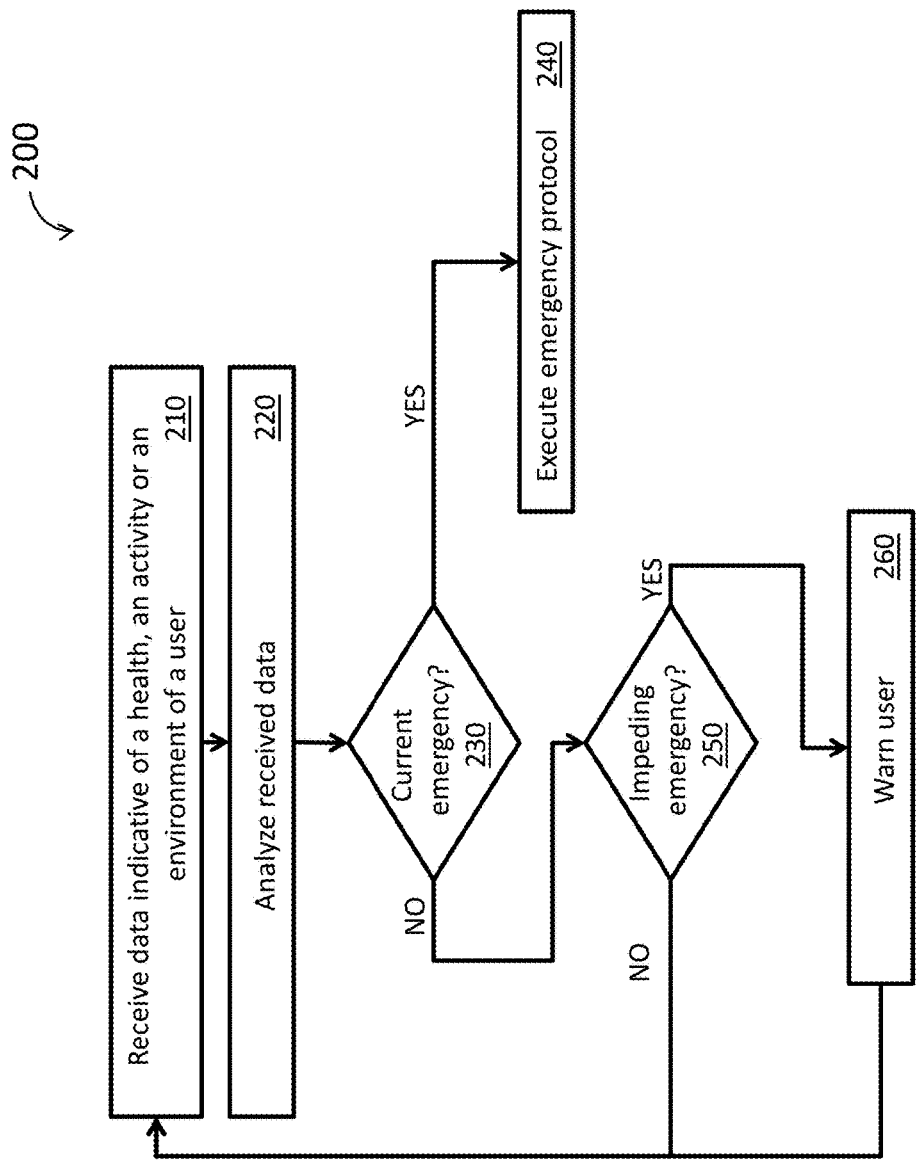
FIG. 2 is a flow diagram depicting an embodiment of a method of detecting and reporting personal emergencies executed by a mobile application.

FIG. 2 is a flow diagram depicting an embodiment of a method 200 of detecting and reporting personal emergencies executed by a mobile application 103 associated with a user. The method 200 can include receiving sensor data, user contextual data, or other data (step 210), analyzing the received data (step 220), checking for a current (or immediate) emergency event (decision block 230), initiating an emergency protocol (step 240) if a current emergency event is detected, and if no current emergency event is detected, checking for an impending emergency event (decision block 250), and warning the user if an impending emergency event is detected (step 260). In some embodiments, the method 200 can be performed by the backend application 120.

The method 200 includes the mobile application 103 receiving sensor data, user contextual data, or other data indicative of the health, activity environment of the user (step 210). The mobile application 103 can receive the sensor data from one or more sensors. The sensors can be sensors embedded in the client device 102, sensors mounted on wearable articles, ambient sensors, sensors associated with medical devices, other sensors or a combination thereof. Sensor data acquired by the mobile application 103 can include motion data, location data, ambient temperature measurements, ambient humidity measurements, medical measurement data (such as user body temperature measurements, user pulse measurements, user heart beat measurement, user blood sugar measurements, user blood pressure measurements or the like), other sensor data (such as chargeability level for batteries associated with medical devices) or a combination thereof.

The mobile application 103 or the backend application 120 can obtain user contextual data such as data related to the user's location (e.g., traffic patterns, air pollution level, etc.), data indicative of a prior user activity, data indicative of changes in user social or economic status (such as divorce, loss of job, death of a family member, public alerts (e.g., weather alerts, crime alters, bacteria or viruses alerts, infectious diseases alerts, etc.) associated with a location or activity of the user, or other user contextual data. The mobile application 103 or the backend application 120 can obtain user contextual data from the user (e.g., as input to the client device 102), the Internet, social media web sites or applications, the user emergency contacts, or other sources. For instance, the mobile application 103 or the backend application 120 can obtain prior activities of the user or social or economic changes through social media content such as feeds or comments made by the user or people in the social media connections of to the user. The mobile application or the backend application 120 can obtain the public alerts data from systems associated with the web service(s) 98 or healthcare provider service(s) 97.

Furthermore, the mobile application 103 or the backend application 120 can receive user medical data (such as medical test results, medical imaging results, prescription information or other user related medical information) from systems associated with the medical provider service(s) 97. In some implementations, the mobile application 103 can prompt the user to enter information indicative of a current activity, select a mode or settings for the mobile application 103 or enter other user-related data. In some implementations, the mobile application 103 or the backend application 120 can infer a current activity of the user or a current mode to be used based on received sensor data or other acquired data. In general, the data acquired by the mobile application 103 or the backend application 120 relates to a state of health of the user, a current activity performed by the user, environment around the user, or a user social, psychological or economic status (or state).

In some embodiments, the backend application 120 can receive sensor data, user contextual data or other data indicative of the health, activity, environment social context, economic context, or psychological context of the user. The backend application 120 can receive the sensor data, user contextual data, user medical data, user activity data, public alerts data, or other user relevant data from the client device 102, systems associated with the web service(s) 98, systems associated with the healthcare provider service(s) 97, the Internet, or other sources. For example, the mobile application 103 can cause the mobile device 102 to send sensor data received from the sensor(s) to the backend system 105. The backend application 120 can have access to user data available (or stored) in the backend system 105.

The method 200 can include the mobile application 103 or the backend application 120 analyzing the received data (step 220). The mobile application 103 or the backend application 120 can store the received data temporarily or permanently. The mobile application 103 or the backend application 120 can be configured to analyze the received data from sensors or other sources using an emergency predictive model. The emergency predictive model can be generated by the backend application 120. The emergency predictive model can include proprietary short term protective analytics for analyzing the input data taking into account any combination of user current condition (such as current health condition(s), current activity, current psychological, social or economic state, location, etc.), environment parameters (available through ambient sensors, the backend application 120, the web service(s) 98 or the healthcare service provider service(s) 97), user settings, past knowledge, and other data to estimate the probability of an impending or current emergency event. In some implementations, the mobile application 103 or the backend application 120 can be configured to compute a probability value (or a score value) indicative of the likelihood of an emergency event currently occurring or about to occur to the user. In some embodiments, the backend application 120 can be configured to perform the analysis of the user data using the emergency predictive model. For instance, the backend application 120 can monitor the connectivity of the client device 102 with the backend system 105, and upon detecting a loss of connectivity, the backend application 120 can analyze sensor data and/or other user related data using the emergency predictive model.

For example, considering motion sensor data, an abrupt drop in motion speed detected by motion sensors can be indicative of the user having a traffic accident and a detected sudden drop in altitude can be indicative of the user failing on the ground. Microphone-recorded loud screams or alarm sounds can be indicative of the user being the subject of a criminal act. Also, sensor measurements indicative of sudden change in user pulse rate or user heart beat rate can be indicative of the user going through a heart attack, a panic attack or other heart related emergency events. Furthermore, a detected low level of charge for batteries associated with a pacemaker, an artificial kidney or other medical device used by the user can be considered a risk that may lead to an emergency event.

Using the received sensor data as well as other data (such user medical data, user location, information related to the surrounding environment, current activity or the like), the mobile application 103 or the corresponding backend application 120 can weigh different risks in computing the likelihood of one or more emergency events. For instance, medical data of the user (such as current/past medical condition(s), current/past medication, user weight, etc.), current activity information or current stress level may influence the likelihood of a heart attack or panic attack. Also, information indicative of a current/past location(s) or current/past activities of the user may lead to increased weights for some risks such as falling, being injured, losing consciousness or being infected by some bacteria or virus. Also, the mobile application 103 or the backend application 120 can modify a weight for some risk of depression, psychological breakdown, or suicide based on information indicative of social or economic changes (such as the loss of loved one or the loss of a job).

Storing the received data can include storing the data locally at the client device 102 or at the backend system 105. The received data can be stored temporarily at the client device 102, for example, for data analysis purposes. Storing the received data can include sending the received data to the backend application 120, through the one or more networks 104, for storage in the backend system 105. The mobile application 103 can be configured to encrypt the received data before sending to the backend application 120. The backend application 120 can be configured to generate/update an emergency predictive model based on the data received from the mobile application 103. Generating the emergency predictive model can further take into account the medical history of the user, the age of the user, the weight of the user, a level of physical activity of the user or other user-related factors. The backend application 120 can be configured to provide the generated emergency predictive model or parameters thereof to the mobile application 103 for use in detecting emergency events associated with the user.

In some embodiments, the backend application 120 can employ the emergency predictive model to detect actual or impending emergency events and notify the user or his/her network about detected actual or impending emergency events. The backend application 120 can include one or more functionalities mirroring functionalities of the mobile application 103. Such functionalities allow the backend application 120 to perform emergency event prediction or detection using sensor data and/or other user data available data, especially in cases where the communication with the mobile device 102 breaks down due to network coverage or power failure.

The mobile application 103 can be configured to communicate regularly with the backend application 120 to update a profile of the user and user-specific processes running on the backend application 120 (such as processes to generate/adapt the emergency predictive model, processes for retrieving data from different sources or other processes). Such regular communications allow the updating of the user's current location, user's current activity, communication network status, battery level of the client device 102 or other user data maintained/monitored by the backend application 120.

The mobile application 103 may also relay information about any backup emergency timer running on the client device 102 to the backend application 120. The backup emergency timers can be used as tools for detecting potential emergency events that may not be detected based on sensor data or other data received available to the mobile application 103 or the backend application 120. For example, when the user is not carrying the corresponding client device 102 (such as when swimming or windsurfing) or when there is a chance of communication disruption or battery failure (such as during a long hiking walk on remote trails) the mobile application 103 may fail to detect or report an emergency event. In such cases, the mobile application 103 allows the user to set a countdown timer to a period of time based on an expected duration of a potentially risky activity. Relaying the timer information to the backend application 120 allows for a similar countdown timer to be running on the backend application 120. The user can abort the timer before it expires to avoid false emergency event detection. If the timer expires without user intervention an emergency notification protocol can be initiated. In some implementations, for each emergency timer set on the client device 102, a corresponding synchronized duplicate timer can be set to run on the backend application 120 for additional safety against temporary or permanent communication failure such as network failure or depleted client device battery. In some implementations, when the duplicate timer expires during a period of communication failure with the mobile application 103, a different version of the emergency notification protocol (different than the version associated with good communication with mobile application 103) can be executed.

The method 200 also can include determining whether a current (or actual) emergency event is occurring to the user (decision block 230). In some implementations, such determination can be achieved by comparing the computed probability or score value to a given threshold value. In some implementations, the given threshold value depends on the state of user. If the computed emergency probability or score value is found to be greater than the threshold value, the mobile application 103 or the backend application 120 can determine that the user is going through a current (or actual) emergency event (decision block 230) and execute an emergency protocol (step 240).

The emergency protocol can include a sequence of actions undertaken by the mobile application 103 or the backend application 120 when a current (or actual) emergency event is detected. In some implementations, the emergency protocol can include two stages; (i) an emergency verification stage and (ii) an emergency reporting stage. During the emergency verification stage, the client device 102 (or the mobile application 103 running thereon) can execute one or more actions to prompt the user to halt the emergency protocol if the detected emergency event is a false alarm. As such, the emergency verification stage allows avoiding, or reducing, false alarms. Also, user feedback (such as halting the emergency protocol) during the emergency verification stage can be used (for example, as training data) to improve the emergency detection capabilities of the system (e.g., the mobile application 103 and the backend application 120) over time. For instance, data associated with false alarms as well as data associated with correctly detected emergency events can be used to improve the emergency predictive model or the user-related processes running on the backend application 120.

Once a current emergency event is detected, the mobile application 103 can prompt the user to halt the emergency protocol during the emergency verification stage. For instance, during this stage, the mobile application 103 can cause the client device 102 to play high pitch sounds and display blinking light or flashlight to attract the attention of the user. Such state (e.g., playing pitch sounds and blinking light or flashlight) can last for few minutes (such as one to ten minutes) depending, for example, on the emergency sensitivity settings. If the user cancels the emergency protocol the mobile application 103 registers the detected emergency event as a false alarm. If the user does not halt the emergency protocol, the mobile application 103 can register the detected emergency event as a valid emergency event. In some implementations, the mobile application 103 may also allow the user to validate the detected emergency event. Information associated with the detected emergency events (such as corresponding input data to the emergency prediction model and information indicative of whether the emergency event is valid or a false alarm) can be used by the backend application 120, for example, as training data to improve the emergency detection model generated for the user.

In some implementations, the mobile application 103 can request user authentication in order to allow the user to halt the emergency protocol. The user authentication can include the user entering a security pin, using fingerprint identification capabilities of the client device 102, or other authentication processes. The use of user authentication in order to allow halting the initiated emergency protocol helps avoiding cancellation of valid emergency events.

If the user does not halt the emergency protocol during the emergency verification stage, the mobile application 103 can start the emergency reporting stage. The emergency reporting stage includes the backend application 120 transmitting a distress signal to emergency contacts (or the safety network) of the user. The backend application 120 can transmit the distress signal to the emergency contact device(s) 107 or to the social network service 99. In some implementations, depending on the type of the user subscription, the distress message can be sent to emergency contacts of the user, the entire safety network of the user, the emergency response service 96, a subset of the user's contacts or an ad-hoc safety network created for a particular occasion. In some implementation, the user may decide to create an ad-hoc safety network in anticipation of certain situations such as traveling abroad where it would be difficult for the user's regular emergency contacts to respond timely. In such cases the user can select from a list of available contacts such as friends of friends or friends of family members willing to watch the user over for a particular period of time. Instead of friends of friends or friends of family members, the user may select other available individuals that are willing to offer their services for free or for a fee. In such cases, the user can be able to see the profiles of such individuals that list specific skills (e.g., "nurse", "fire fighter", "emergency responder", "knows CPR", etc.), availability, rating from previous engagements with other users, fees per period, etc., and contract the one(s) that fits best the requirements at hand. In some implementations, the ad-hoc safety network can be formed when a current emergency event is detected based on proximity of the contacts to the user, user's relations (e.g., "family," "friend," "close friend," etc.) to the corresponding contacts, user preferences or other criteria. The distress signal can include information such as (i) a standard or a customized message to the recipients, (ii) indication of the last known location and direction of the user, (iii) indication of the last known type of activity of the user (such as walking, running, driving, etc.), (iv) information indicative of the user's medical condition and medication, (v) other user social or physiological data, or a combination thereof.

In some implementations, once the distress signal has been sent, the mobile application 103 can cause the client device 102 to enter a protected mode. In the protected mode, the screen of the client device can display the basic personal information of the user while being locked in order to avoid accidental cancellation of the emergency protocol. The client device 102 can also beep periodically when in the protected mode and relay information to the backend application 120 periodically in an effort to optimize battery usage. Once emergency responders arrive, they can read the user's displayed information and treat the user accordingly.

In some implementations, depending on characteristics of the client device 102 or a subscription level of the user, the distress signal can be an automated short message service (SMS) message. Some types of client devices 102 (such as client devices 102 employing the iOS operating system), do not allow automatic transmission of SMS messages due to security restrictions. For such client devices, automatic SMS messaging can be provided through third-party messaging applications.

In some implementations, the distress signal can include information indicative of the detected emergency event in plain text. In such implementations, the distress signal can include an iMessage message, SMS message, email, social network post, message to other users of the emergency detection and reporting system, or the like. In some implementations, the distress message can include a temporary uniform resource locator (URL). In such implementations, sensitive (in terms of privacy) information of the user (such as medical condition(s) information or other personal information) can be posted on the URL. Access to the URL can include credential(s) authentication. The credential(s) can include a pin, password, or other authentication information. Using credential authentication allows access to sensitive data of the user to be limited to a subset of contacts of the user that have the proper credentials. In some implementations, the credential(s) can be shared by the user with a subset of the corresponding emergency contacts or members of the safety network prior to the detection of the emergency event. In some implementations, the credential(s) can be automatically sent (as part of the emergency protocol) to the subset of contacts of the user through separate message(s). Besides using credential(s) authentication to restrict access to the sensitive data, the URL can be configured to exist temporarily in order to mitigate access to the sensitive data of the user by unauthorized intruders. For instance, using a temporary URL prevents the sensitive data from becoming part of the Internet archives (not searchable, cached, etc.). In addition, the use of temporary URL can protect against spreading the sensitive information in case of false alarm. For instance, if the emergency protocol is cancelled, the cancellation process can include removing the temporary URL.

If no current emergency event is detected (decision block 230), the mobile application 103 or the backend application 120 can check for an impending emergency event (decision block 250). In some implementations, the mobile application 103 can compare the previously computed probability or score value (used to detect current emergency event(s)) to a second threshold (e.g., smaller than the threshold used to detect current emergency event(s)). In some other implementations, the mobile application 103 or the backend application 120 can compute a second probability or score value (different than the one used to detect current emergency event(s)) and compare the second probability or score value to a second threshold. Examples of impending emergency events can include detected low battery charge associated with a medical device used by the user, abnormal medical test values, detecting risks (e.g., based on obtained public alerts) associated with a user location or user event, detected risky driving (e.g., detected driving speed exceeding substantially speed limit or detected zig-zag motion while driving) or the like.

Upon detecting an impending emergency event (decision block 250), the mobile application 103 or the backend application 120 can be configured to display a warning message to the user on a display of the client device 102. The mobile application 103 can also cause the client device to output a sound, a flashing light, or other output signal to attract the attention of the user. The warning message can include information describing the detected impending emergency event, one or more suggestions to the user, a link with further information to the user, or the like.

In some implementations, checking for an impending emergency event (decision block 250) can occur prior to checking for a current emergency event (decision block 250). In some other implementations, a single check can be performed to detect for impending and current emergency event(s). For instance, depending on a computed probability or score value, the mobile application 103 can determine which emergency event, if any, is highly likely.

Upon detecting an impeding emergency event (decision block 250), the mobile application 103 or the backend application 120 can send a warning message (or notification) to the user indicative of the impeding emergency event to occur (step 260). The notification can include an instruction (or request) for the user to change a given behavior to avoid the predicted emergency event. For instance, if reckless driving is detected, the notification can include a request for the user to slow down or drive safely. If sensor data indicates consistently high blood pressure and/or irregular heartbeat, the notification can include an request for the user to urgently seek medical help. The mobile application 103 or the backend application 120 can monitor the user behavior (e.g., by monitoring user location, user motion and/or speed, or other sensor data). If the mobile application 103 or the backend application 120 detects (e.g., through monitoring sensor data or other data indicative of user behavior) that the behavior of the user did not change (e.g., based on location and/or motion information data, the user driving did not change or the user did not go to a healthcare service facility to seek medical help), the mobile application 103 or the backend application 120 can initiate reporting the predicted emergency event to an emergency contact of the user or a contact within a social safety network of the user. In reporting the predicted emergency event, the mobile application 103 or the backend application 120 can include a description of the predicted emergency event, indication of the user location, or other relevant information. In some embodiments, the mobile application 103 or the backend application 120 can send a distress signal to an emergency contact of the user, an emergency response service, or an ad-hoc safety network created by the user.

In some embodiments, either the detection of actual emergency event (decision block 230 and step 240) or the detection of an impeding emergency event can be optional. In some embodiments, the mobile application 103 or the backend application 120 can be configured to execute a first method for detecting and reporting actual emergency events and/or a second method for detecting and reporting impeding emergency events.

Figure 3:
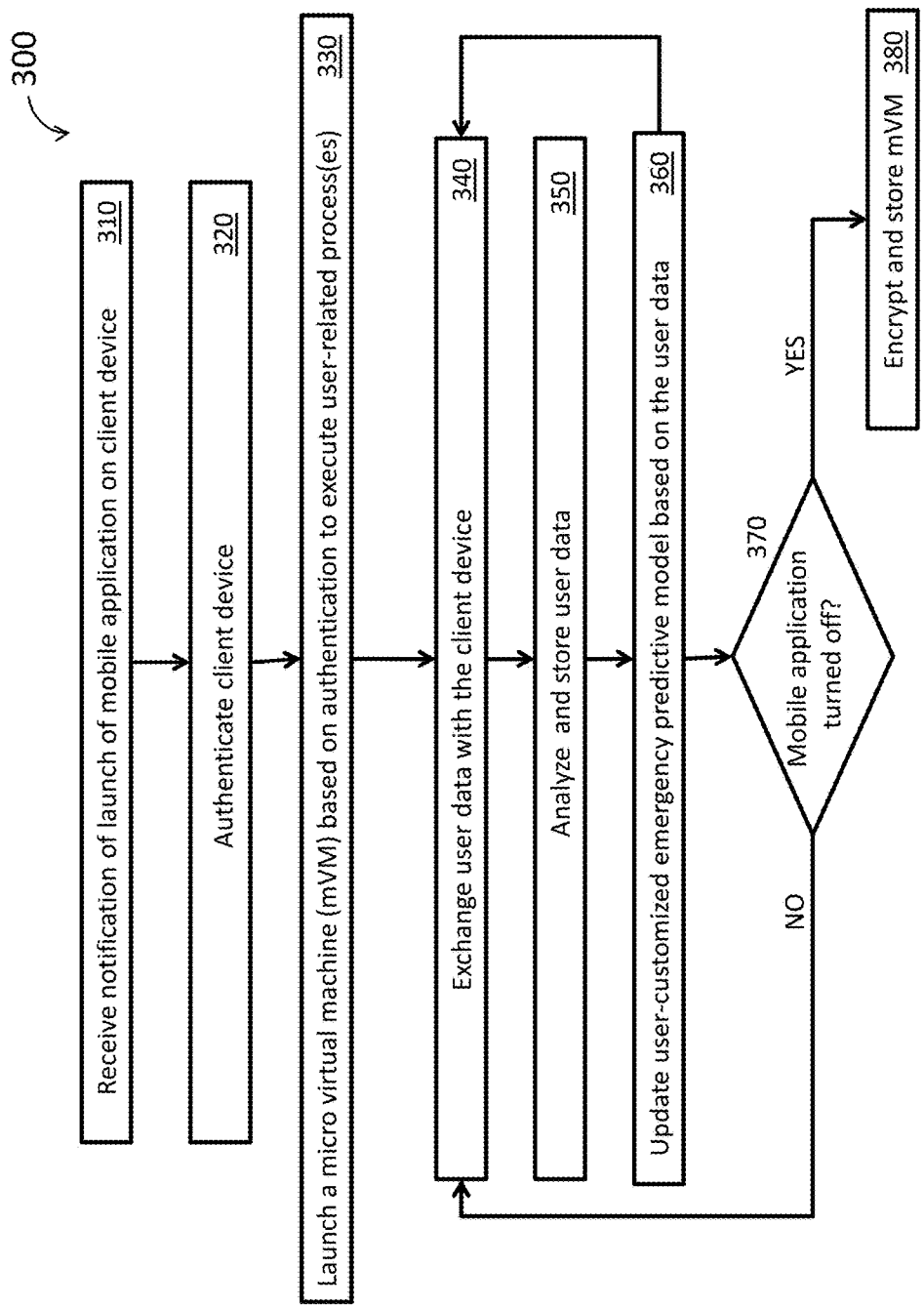
FIG. 3 is a flow diagram depicting an embodiment of a method executed by a backend system for detecting and reporting personal emergencies

FIG. 3 is a flow diagram depicting an embodiment of a method 300 executed by the backend application 120 for detecting and reporting personal emergencies. The method 300 includes receiving a notification indicative of launch of mobile application 103 on client device 102 (step 310), authenticating the client device 102 or the corresponding user (step 320) and launching a micro virtual machine (mVM) 129 to execute user-related process(es) (or algorithms) (step 330). The method 300 also includes exchanging user-related data with client device 102 (step 340), analyzing and storing received user-related data (step 350) and updating the user customized processes based on the received user-related data (step 360). The method 300 further includes encrypting and storing the mVM 129 (step 380) upon detecting that the mobile application 103 is turned off on the client device (decision block 370).

The method 300 includes the backend application 120 receiving a notification indicative of launch of the mobile application 103 on the client device 102 (step 310). For instance, when the user of the client device 102 starts the mobile application 103 (or if the mobile application 103 is automatically launched when the client device 102 is turned on), the client device 102 transmits information to the backend application 120 indicating that the mobile application 103 is started on the client device 102. Such information can include an identification of client device 102, an identification of the mobile application 103, an identification of the user, a phone number associated with the client device or a combination thereof.

The method 300 includes the backend application 120 authenticating the client device 102 on which the mobile application 103 is launched (step 320). In some implementation, during setup of the mobile application 103 on the client device 102, the client device 102 can prompt the user to create a new account and enter authentication parameters (such as username, password, security questions or a combination thereof), email accounts information, a primary mobile phone number to be used and some extra security options (such as other information for data encryption, data recovery, data backup, two factor authentication or the like). In response, the backend application 120 can confirm the email account(s) and primary mobile phone number (associated with the client device 102) of the user. The confirmation of the email account(s) can be achieved by the user clicking a link automatically sent by the backend application 120 to the email account(s) of the user. The confirmation of the mobile phone number can be achieved by sending an SMS message including a code (e.g., multi-digit string) to the mobile phone associated with primary mobile phone number and asking the user enter the same code on a web page associated with the backend application 120. Once the confirmation is completed, the user can continue the setup process (e.g., entering personal profile information, connections information, privacy levels information, timeframe and scope of data repository functionality, authentication on other social networks, etc.) either through a web page associated with the backend system 105 or on the device 102.

In some implementations, the authentication process (step 320) includes authenticating the phone number associated with the client device. In some implementations, the backend application 120 can further request other authentication information (such as login and password, a pin, biometric authentication of the user on the client device 102 or other user authentication information) as part of the authentication process in step 320. In some implementations, the primary mobile phone number of the user can serve as a unique identifier of the user on the backend system 105. Upon successful authentication at step 320, the mobile application 103 launched on the client device 102 can be connected to the backend system 105 through the one or more networks 104 and the user is provided access content on the backend system 105. In some implementations, based on privacy settings of the user, the backend application 120 can broadcast to one or more other users a unique identifier of the user upon successful authentication at step 320.

In some implementations, a user may use more than one phone number (e.g., primary and secondary phone numbers). In some implementations, a secondary authentication process can be deployed when the secondary phone number is used for authentication at step 320. The secondary phone number may be associated with a second client device of the user or the same client device using a second SIM card. The secondary authentication process can include the backend application 120 sending a key (e.g., a multi-digit string) to be keyed on the mobile application 103 running on the client device associated with the secondary mobile phone number. The client device associated with the secondary mobile phone number can connect to the backend system 105 using the key and other user authentication information (such as username and password). Also, if a user changes a corresponding primary phone number, an "authentication transfer" process can be employed. In some implementations, such process can be similar to the secondary authentication process for secondary phone numbers. Also, once a new mobile phone number has been authenticated as secondary, the user may select to change it as the primary mobile phone number.

In some implementations, the notification step (step 310) and the authentication step (step 320) can be implemented as a single step. For instance, upon launch of the mobile application 103, the client device 102 can send an authentication request to the backend system 105. Such request can be interpreted by the backend system as a notification of launching the mobile application 103 on the client device 102 (step 310) and can also be used to authenticate the client device 102 based on information in the request (step 320). In some implementations, based on the user settings, the client device 102 can further send other information in (or with) the authentication request (such as the type of user subscription or indication(s) of power optimization algorithms) to the backend application 120.

The method 300 also can include the backend application 120 launching a micro virtual machine (mVM) 129 to execute user-related processes or algorithms (step 330) upon successful authentication at step 320. The use of the mVM 129 allows protection of user-related data (such as user personal information, user medical data, algorithms specific to the user, etc.) stored in the backend system 105 so that such data is not accessible (in unencrypted format) to others including operators or administrators of the backend system 105. In some implementations, such data protection can be employed based on user specific preferences. For instance, the user can choose such data protection procedure through selection of security/privacy preferences. In some implementations, the mVM 129 can encapsulate both the user specific data and customized instance(s) of algorithm(s) used to analyze user data, generate/adapt emergency predictive model(s) for the user or perform other user-customized processes. The mVM 129 is started once the mobile application 103 is activated on the client device 102 and the client device is authenticated (step 320). In some implementations, the client device 102 provides the backend application 120 with a private key specific to the user used in launching the mVM 129. In some implementations, if the client device 102 includes biometric authentication capabilities or other security capabilities, the key can be automatically sent by the client device. In some other implementations, the mobile application 103 employs other verification process(es) to authenticate the user before sending the private key to the backend application 120.

In some implementations, the mVM 129 can be running on a micro-virtual server with a corresponding unique Internet protocol (IP) address. The IP address of the micro-virtual server can be (i) randomly set at initiation and (ii) renewed at random intervals during the period the mVM 129 instance is running. Also, the client device 102 can perform handshaking through the backend system 105 (when communicating with the backend application 120) to prevent intruders from routing back from the backend system 105 to the client device 102 and therefore associating the data (associated with the running mVM 129) to the user. The use of the mVM 129 enhances security and privacy of user data. Specifically, the use of the mVM 129 mitigates the risk of the user data being traced or accessed by others. As such, the user can export corresponding user data from the backend system 105 with little or no risk of breaching user privacy by others. If the user decides to delete the corresponding data from the backend system 105, the encrypted data will be deleted permanently with no copies left on the backend system 105, therefore, avoiding (or mitigating) the risk of tracing or accessing the user data by others.

The method 300 can include the backend application 120 exchanging user-related data with the client device 102 through the one or more networks 104 (step 340). Exchanging the user-related data can include synchronizing data between the backend application 120 and the mobile application 103 upon successful authentication of the client device 102 at step 320. If the client device 102 is authenticated by the backend system 105 (step 320) based on a secondary phone number and is different from a client device associated with the primary phone number, the synchronization process can take longer as more data may be exchanged. Exchanging the user-related data (step 340) also includes the backend application 120 receiving sensor data from the mobile application 103. Exchanging the user-related data (step 340) also includes the backend application 120 sending information indicative of the emergency predictive model or parameters thereof, information obtained from system(s) associated with the healthcare provider service(s) 97, web service(s) 98 or social network service(s) 99 to the mobile application 103.

The method 300 also includes analyzing and storing user-related data (step 350). The backend application 120 can be configured to collect various information related to the user such as sensor data received from the client device 102, user activity information, user location information, user medical information, public/news alerts, information posted by the user or contacts of the user on the social network service(s) 99, or a combination thereof. The mobile application 103 can analyze such data, for example, to identify new risks, new condition(s) or any new information relevant to the user. For instance, the backend application 103 can compare and filter the collected data based on previously stored data for the user, Analyzing the user-related data (step) 350) can include updating (or computing) statistical data specific to the user based on newly acquired data by the backend application 120. Analyzing the data (step 350) can also include identifying and retrieving other information based on obtained user-related data. For example, if recently obtained user-related information is indicative of a new medical condition, new activity, or new location, the backend application 120 can retrieve further information or other algorithms (from a database or other sources) to identify or assess risks associated with such new medical condition, new activity, or new location.

The backend application 120 is also configured to store the user-related data in the backend system. Storing the user-related data can include encrypting and storing an encrypted version of the data. The encrypted data can be backed on regular intervals in order to ensure availability of service in case of disaster. Also, the backend application 120 can strip some of the user data from any personal data (such as name, phone number or email) that can identify the owner of the data, and, store the modified data in the backend system 105 for use in research or to improve generic (non-user specific) algorithms or processes used in the backend system 105. The user can choose to keep corresponding logged data permanently on the backend system 105, to set specific periods for resetting the data, or not to log data in the backend system 105.

The method 300 also includes the mVM 129 updating a user-customized emergency predictive model based on the acquired user related data (step 360). In some implementations, the emergency predictive model can be a neural network, a finite state machine, other mathematical model, a software module or a combination thereof. In some implementations, the emergency predictive model can be configured to receive user data (such as sensor data, user medical, location data, activity data or a combination thereof) as input and provide an output indicative of whether an emergency event (and type of event) is highly likely based on the input data. The emergency predictive model, can be customized to the user in terms of corresponding input data, internal parameters (such as weighting coefficients, thresholds or the like), or mathematical model(s) employed. For instance, the input to the emergency predictive model can depend on sensors available to the client device 102, medical condition (s) of the user, or other user-specific information. Internal parameters of the emergency predictive model also depend on user specific information.

In some implementations, the mVM 129 is configured to use collected (or filtered) user-related data to train, update or adapt the emergency predictive model for the user over time. The more data available and the longer that data is available to protective analytics running on the mVM 129, the better the predictive accuracy of the emergency predictive model can get. If the user chooses not to maintain corresponding data at all in the backend system, the corresponding emergency predictive model can be generated (or trained) based mainly on generic (non-user specific) data, which can degrade the corresponding accuracy. Also initially, the emergency predictive model can be generated based mainly on the generic data. Once the emergency predictive model is updated, the backend application 120 sends information indicative of the updated model or parameters thereof to the mobile application 103. For example, if the emergency predictive model includes a neural network, the backend application 120 can send updated parameters of the neural network to the mobile application 103. In some implementations, the emergency predictive model can be executed on the mVM 129 and the backend application 120 can send emergency prediction results to the mobile application 103.

Upon detecting that the mobile application 103 is turned off on the client device 102 (decision block 370), the backend application 120 can abort the mVM 129 from running, encrypt an instance of the mVM 129 (and any related data) and store the encrypted instance (step 380) for use when the mobile application 103 is back on.

The backend application 120 can be configured to provide a long term secure repository for the user's sensitive information including but not limited to activity, biometrics, medical, medication, or other information. The backend application 120 can serve as a communication hub that connects the client device 102 with the user's social safety network and relays emergency signal(s) if and when needed along with other relevant information. The backend application 120 can serve as a computational engine that uses long term protective analytics to crunch user specific data, combine the data with other relevant information available through the internet (location specific, time specific, condition specific, etc.) and estimate the probability of long term emergencies. The backend application 120 can serve the client device 102 with relevant information (location, time and condition based) in order to support the short term protective algorithms running on the client device 102. The backend application 120 can serve the client device 102 with relevant information (location, time and condition based) in order to help the user make decision and take action related to personal safety (for instance finding the closest police station or hospital). The backend application 120 can notify the user about an impending or actual emergency of another member in the social safety network of the user. The backend application 120 can provide the user with information about the availability and proximity of other members in the safety network of the user. Such feature can depend on the privacy settings of the user and corresponding peers and can eventually allow to setup ad hoc social security networks.

FIGS. 4A-4D show various screenshots 400a-400b of a user interface of a client application for detecting and reporting personal emergencies. The user interface can include a map 401 indicative of the user location, a user profile and settings icon 402, a search icon 404, a timer icon 406, a social safety network icon 408, and an emergency button 405.

Figure 4A:
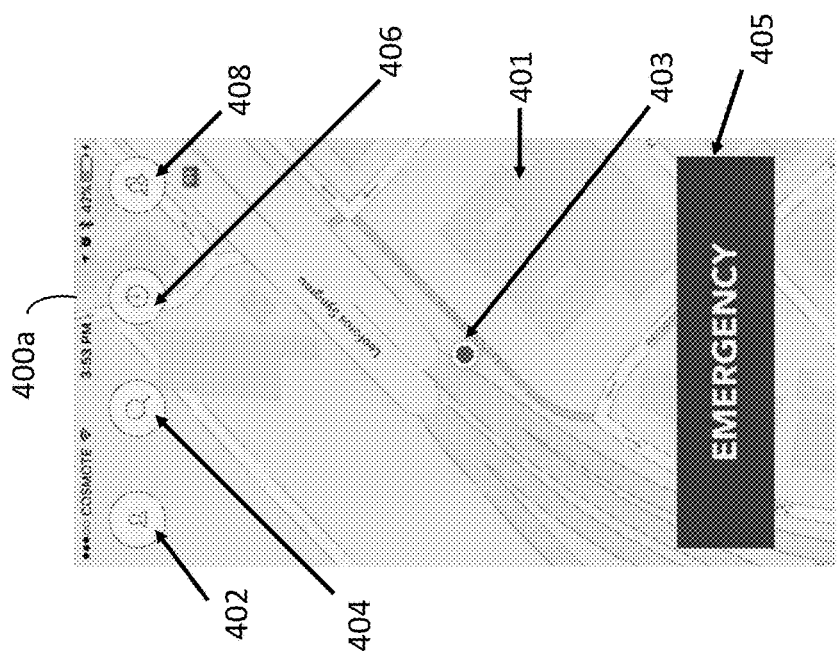

Referring to FIG. 4A, the map 401 can show a geographic area associated with the user location. In some embodiments, the map 401 can include a graphical pointer 403 (such as a dot or other graphical feature) indicative of the user's location on the map 401. The user profile and settings icon 402 can allow the user to set up, view, or modify a user profile and user settings. The user profile can include information such as the name of the user, user home address, user age, user email address, other information or a combination thereof. User settings can include information indicative of privacy settings, emergency sensitivity settings, display settings, or other settings information. The search icon 404 allows for searching for points of interest in the vicinity of the user (such as hospitals, healthcare service institutions, etc.), saved locations (such as user home), or other locations based on respective addresses. The timer icon 406 allows the user to set up a safety timer (such as when performing an activity that may involve some risk). The social safety network icon 408 allows the user to set up, view, or modify a social safety network. The user can use the social safety network icon 408 to add, delete or modify information of emergency contacts within a social safety network.

Referring to FIG. 4B, the user can actuate (e.g., by pressing) the emergency button 405 to manually call for help. As shown in FIG. 4B, the color, brightness or appearance of the emergency button can change upon actuation of the button. Upon actuating an emergency button 405, the mobile application 103 can send a distress signal (e.g. to an emergency contact of the user) or can initiate a phone call (such as a 911 call or a call to an emergency service facility). In some embodiments, the mobile application 103 can wait for a short time period (such as 10 seconds, 30 seconds, 1 minute, or other time period) before sending the distress signal or initiating an emergency call upon actuation of the emergency button 405. The user interface can display the time remaining till the distress signal is sent or the emergency call is initiated. In some embodiments, the user interface can display a shrinking bar 407 as an indication of the time remaining.

Referring to FIG. 4C, illustrated is a panned and zoomed version of the map 401. The user interface can be configured to allow panning and zooming of the map 401. In some embodiments, the user interface can provide a map resetting icon 409 (or actuation item) to center the map 401 around the current user location. If the user actuates the map resetting icon 409, the user interface changes the map to reflect a geographical region centered at the current user location.

Figure 4D:
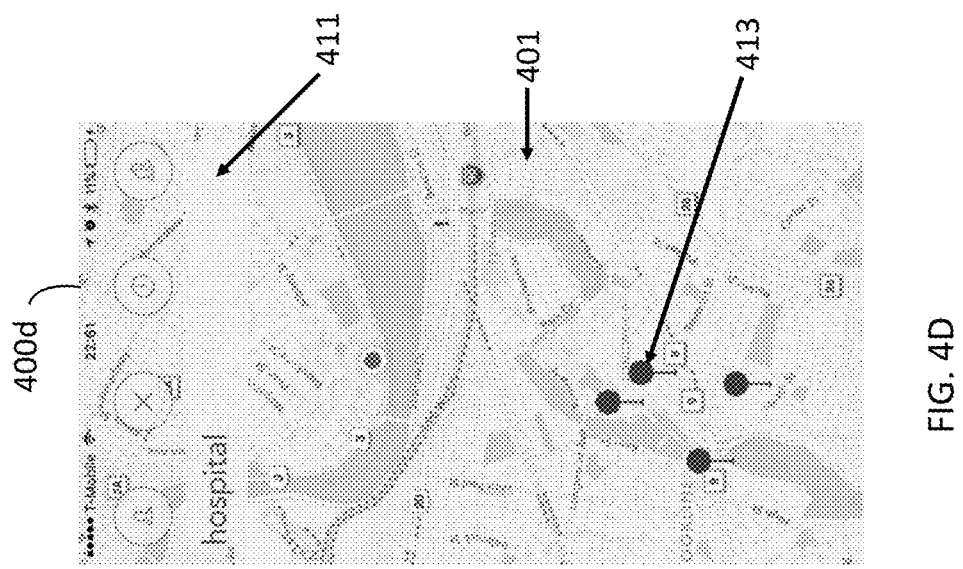

Referring to FIG. 4D, illustrated is a screenshot of the user interface (or the map) upon performing a search for a point of interest. Upon actuating the search icon 404 by the user, the user interface can display a search window 411 where the user can enter a point of interest or an address. For example, the user can enter the term "hospital," in which case the user interface displays hospitals in the vicinity of the user. Responsive to the search, the mobile application 103 and the user interface can identify and display one or more graphical pointers (or pins) 413 indicative of locations of facilities (or buildings) matching the search term (e.g., hospitals). As illustrated in FIG. 4D, the user interface can change the displayed map view based on the location(s) of the identified points of interest (e.g., hospitals).

Although implementations of the systems and methods of the present disclosure have generally been discussed in connection with an emergency predictive model running on the client device 102 or the backend system 105, more than one emergency predictive model can be employed per user. For instance, a short term emergency predictive model can be executed by the client device while a long term emergency predictive model can be running on the mVM 129 (or the backend system 105 in general). The long term emergency predictive model can predict/detect potential future emergency events (or risks) and warn the user or provide advice(s).

While the present solution has been particularly shown and described with reference to specific embodiments, it should be understood by those skilled in the art that various changes in form and detail may be made therein without departing from the spirit and scope of the invention described in this disclosure.

While this specification contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed:

1. A method for predicting an emergency event is to occur to a user, the method comprising:
    (a) generating, by a micro-virtual machine (mVM) executed by the server, a user-customized emergency predictive model using, at least in part, user-specific data;
    (b) launching, by the server, the mVM upon determining that a mobile application is activated on a mobile device;
    (c) receiving, by the mobile device, data about at least one of a health, an activity or an environment of the user;
    (d) analyzing, by one of the mobile device or the server, using the user-customized emergency predictive model, the data about at least one of the health, the activity or the environment of the user;
(e) determining, by one of the mobile device or the server, from the analyzed data and using the user-customized emergency predictive model, a score value indicative of a likelihood of an emergency event occurring to the user; and
(f) communicating, by one of the mobile device or the server responsive to the score value being greater than a threshold, a notification to the user to change behavior to avoid the emergency event; and
(g) encrypting, by the server, the mVM upon detecting that the mobile application is turned off on the mobile device, the mVM encapsulating the user specific data.

2. The method of claim 1, further comprising detecting, by one of the mobile device or the server, that the behavior of the user did not change and responsive to the detecting initiating, by one of the mobile device or the server, emergency reporting.

3. The method of claim 2, further comprising sending, by one of the mobile device or the server, a distress signal to one or more of the following: emergency contacts of the user, an emergency response service or an ad-hoc safety network created by the user.

4. The method of claim 1, wherein the data comprises contextual data about the user and data from one or more sensors associated with the user.

5. A system for predicting an emergency event is to occur to a user, the system comprising:
a mobile application configured to be executable on a mobile device to receive data about at least one of a health, an activity or an environment of the user;
a server configured to communicate with the mobile application and receive data from the mobile device;
wherein the server is configured to:
execute a micro-virtual machine (mVM) to generate a user-customized emergency predictive model using, at least in part, user-specific data; and
launch the mVM upon determining that a mobile application is activated on the mobile device; and
encrypt the mVM upon detecting that the mobile application is turned off on the mobile device, the mVM encapsulating the user specific data, and
wherein at least one of the mobile application or the server is configured to:
receive data about at least one of a health, an activity or an environment of the user;
analyze, using a user-customized emergency predictive model, the data about at least one of the health, the activity or the environment of the user;
determine, from the analyzed data and using a user-customized emergency predictive model, a score value indicative of a likelihood of an emergency event occurring to the user; and
communicate, responsive to the score value being greater than a threshold, a notification to the user to change behavior to avoid the emergency event.

6. The system of claim 5, wherein one of the mobile device or the server is further configured to detect that the behavior of the user did not change and responsive to the detecting initiating, by one of the mobile device or the server, emergency reporting.

7. The system of claim 6, wherein one of the mobile device or the server is further configured to send responsive to the detection a distress signal to one or more of the following: emergency contacts of the user, an emergency response service or an ad-hoc safety network created by the user.

8. The system of claim 5, wherein the data comprises contextual data about the user and data from one or more sensors associated with the user.

9. The method of claim 1 further comprising:
providing, by the server, at least one parameter of the user-customized emergency predictive model to the mobile device.

10. The method of claim 1 further comprising:
updating one or more parameters of the user-customized emergency predictive model using the received data about at least one of the health, activity or environment of the user.

11. The method of claim 3, wherein the distress signal includes a uniform resource locator (URL).

12. The method of claim 11, wherein access to the URL is limited, via credential authentication, to one or more of the emergency contacts of the user, the emergency response service or the ad-hoc safety network created by the user.

13. The system of claim 5, wherein the server is further configured to:
provide at least one parameter of the user-customized emergency predictive model to the mobile device.

14. The system of claim 5, wherein the server is configured to:
update one or more parameters of the user-customized emergency predictive model using the received data about at least one of the health, activity or environment of the user.

15. The system of claim 7, wherein the distress signal includes a uniform resource locator (URL).

16. The system of claim 15, wherein access to the URL is limited, via credential authentication, to one or more of the emergency contacts of the user, the emergency response service or the ad-hoc safety network created by the user.

* * * * *